(12) United States Patent
Folestad et al.

(10) Patent No.: US 7,219,568 B2
(45) Date of Patent: May 22, 2007

(54) APPARATUS AND METHOD FOR ANALYSING

(75) Inventors: Staffan Folestad, Västra Frölunda (SE); Kurt Lundström, Skellefteå (SE); Göran Östling, Rönninge (SE)

(73) Assignee: AstraZeneca AB, Södertälje (SE)

( * ) Notice: Subject to any disclaimer, the term of this patent is extended or adjusted under 35 U.S.C. 154(b) by 95 days.

(21) Appl. No.: 09/806,801

(22) PCT Filed: Jan. 26, 2001

(86) PCT No.: PCT/SE01/00159
§ 371 (c)(1), (2), (4) Date: Apr. 4, 2001

(87) PCT Pub. No.: WO01/57500
PCT Pub. Date: Aug. 9, 2001

(65) Prior Publication Data
US 2002/0125434 A1    Sep. 12, 2002

(30) Foreign Application Priority Data
Jan. 31, 2000    (SE) .................................... 0000314

(51) Int. Cl.
*G01N 35/10*    (2006.01)
(52) U.S. Cl. .................................................. 73/864.81
(58) Field of Classification Search .................. 73/863, 73/865.8, 866
See application file for complete search history.

(56) References Cited

U.S. PATENT DOCUMENTS

| | | | | |
|---|---|---|---|---|
| 3,521,963 A | * | 7/1970 | Bader | .......................... 356/244 |
| 4,286,881 A | * | 9/1981 | Janzen | ........................ 356/440 |
| 4,319,269 A | * | 3/1982 | Kajiura et al. | ................ 348/92 |
| 4,472,960 A | * | 9/1984 | Motoyama et al. | ........... 73/865 |
| 5,463,223 A | * | 10/1995 | Wong et al. | ............ 250/339.12 |
| 5,661,249 A | | 8/1997 | Rupp et al. | |
| 5,679,954 A | | 10/1997 | Soloman | |
| 5,999,253 A | | 12/1999 | Langkilde | |
| 6,014,212 A | * | 1/2000 | Hammond et al. | ......... 356/319 |
| 6,244,118 B1 | * | 6/2001 | Andersson et al. | ...... 73/863.52 |
| 6,275,294 B1 | * | 8/2001 | Folestad | ..................... 356/432 |

FOREIGN PATENT DOCUMENTS

DE    4441686    6/1995

(Continued)

*Primary Examiner*—Hezron Williams
*Assistant Examiner*—Paul M. West
(74) *Attorney, Agent, or Firm*—White & Case LLP (57) ABSTRACT

The present invention relates to a sample presentation apparatus for use in analyzing equipment for pharmaceutical products, for example solid dosage forms such as a tablet, a pellet or a capsule. The invention further relates to a method for presentation of samples to the analyzing equipment. Samples are sequentially fed through at least one predetermined analyzing position (6) wherein at least one measuring radiation beam irradiates the sample (14) when it is located in the analyzing position characterized in that there is at least one two-piece means (9, 39) for temporarily fixing each sample at said analyzing position (6), the two-piece means comprises a first and a second sample holding part arranged at the analyzing position in which the two-piece means is adapted to move between
- an open position wherein a sample is provided for analysis, and
- a closed fixing position wherein a sample is analyzed.

25 Claims, 11 Drawing Sheets

FOREIGN PATENT DOCUMENTS

| | | |
|---|---|---|
| EP | 0322611 | 7/1989 |
| EP | 436338 A2 * | 7/1991 |
| EP | 0767369 | 4/1997 |
| EP | 0896215 | 2/1999 |
| FR | 2762678 | 10/1998 |

* cited by examiner

APPARATUS AND METHOD FOR ANALYSING

TECHNICAL FIELD OF THE INVENTION

The present invention relates to a sample presentation apparatus for use in analysing pharmaceutical products, for example solid dosage forms such as a tablet, a pellet or a capsule. The invention further relates to a method for presentation of samples to a sample presentation apparatus as well as the use thereof.

BACKGROUND OF THE INVENTION

Non-invasive, non-destructible analysis of whole tablets can be carried out by means of near-infrared (NIR) or Raman spectrometry. The common feature of both these techniques is that they utilise light in the NIR wavelength region (700–2500 nm, specifically 700–1500 nm) where pharmaceutical tablets is several millimetres and information on the content can be obtained from the inside of the tablet and not only from the surface. Measurements on a solid dosage form such as a tablet, a pellet or a capsule, are conducted to obtain information for example on the concentration of the active drug and/or the concentration of non-active components or their spatial distribution, i.e. homogeneity. In particular, it is of interest to monitor the quality consistency of doses during the manufacturing process. Thus, real-time measurements during the manufacturing process, for example during the tabletting process, may reveal important information to be used for controlling the process.

Typically, the prior-art tablet analysers acquire a spectrum for each tablet being analysed during an analysing time period when the sample is positioned in the measuring or analysing light beam. To this end, optical tablet analysers conventionally comprise some sort of tablet positioning unit for presentation of one tablet at a time to the analysing beam(s). Firstly, the prior art includes single-tablet positioning units; i.e. positioning units that can support only one tablet at a time, namely the tablet being analysed. Secondly, the prior art includes multiple-tablet positioning units arranged to hold multiple tablets at a time for performing multiple spectrometric measurements by sequentially presenting the tablets to the analysing beam(s).

EP 0767 369 A discloses an apparatus for NIR transmission measurements of tablets containing pharmaceutical compounds. An object of this apparatus is to minimise or eliminate the incidence of stray light reaching the detector and therefore, a sample locator is used together with a masking device. The sample, a tablet, is positioned in a cylindrical well within the locator and thereafter an annular masking element is placed within the well to engage the top surface of the tablet. In this way the possibility that light will leak around the sample is minimised. One embodiment comprises a single-tablet holder having only one single-tablet receiving well for performing a single-tablet analysis. Another embodiment comprises a multiple-tablet holder in the form of a rotating plate provided with several tablet-receiving wells spaced circumferentially on the rotating plate for performing a multiple-tablet analysis of a predetermined number of tablets.

The insertion of the tablets into each well has to be done manually prior to the analysis. Therefore, the number of analyses is limited to the number of wells in the sample locator, which precludes its use for continuous automated analysis. A further drawback is that due to different physical parameters of each well, such as tolerances, dimensions, surface finish etc., the wells of a given plate will not be mutually identical. This fact will introduce imprecision in the analysis.

DE 4441686 A relates to an apparatus for testing tablets. From a batch source containing tablets to be tested, tablets are transported via a vibrating table down to a sloping table from which the tablets fall onto a rotating testing plate comprising drilled cavities to receive tablets. The tablets are exposed to a light beam from a light source hanging above the testing plate and a detector is placed under the testing plate.

In this prior art device a continuously automated analysis can be performed. However, due to different physical parameters of each cavity, such as tolerances, dimensions, surface finish etc., the cavities will not be identical. This fact will introduce imprecision in the analysis. Further, vibrations from the vibrating table are likely to effect the rotating test plate. These vibrations will disturb the on-going measurements.

SUMMARY OF THE INVENTION

A general object of the present invention is to solve or alleviate some or all of the problems described above. More specifically, the apparatus and method according to the invention should allow for performance of an optical measurement(s) on a pharmaceutical sample with high accuracy, precision and reliability.

A further object of the invention is to perform continuous and automated measurements of pharmaceutical samples preferably connected on-line to a tabletting process, especially a system that is not limited to a certain number of samples and, therefore, allows a high sample capacity.

Another object of the invention is to make possible an optical measurement where the amount of manual sample handling is eliminated or at least reduced.

According to one aspect of the present invention there is provided a sample presentation apparatus for use in analysing pharmaceutical samples, comprising means for feeding said samples sequentially through at least one predetermined analysing position wherein at least one measuring radiation beam irradiates said sample when it is located in said analysing position characterised in that there is at least one two-piece means for temporarily fixing each sample at said analysing position, said two-piece means comprising a first and a second sample holding part arranged at said analysing position in which said two-piece means is adapted to move between an open position wherein a sample is provided for analysis, and a closed fixing position wherein a sample is analysed.

Preferably, the first and second sample holding parts, each defining an aperture are located on opposite sides of the sample in the analysing position. When a sample is being analysed in the closed fixing position the two apertures, one in each sample holding part, define an effective optical aperture.

To make sure that the sample reaches the analysing position in the correct three-dimensional position in space, the sample is pre-aligned before entering the analysing position. Preferably, the means for feeding samples sequentially through the analysing position comprises at least one pre-alignment means for receiving and holding a sample during the transport thereof to the analysing position. In one embodiment, the pre-alignment means comprises an elastically compressible member such that the sample is flexible engaged in the pre-alignment means. In another embodiment, the pre-alignment means comprises a spring-loaded arm that embraces the sample.

Preferably, the means for feeding samples sequentially through an analysing position is represented by a rotating wheel comprising at least one pre-alignment means for receiving at least one sample.

In another aspect, the present invention provides a method for presenting pharmaceutical samples to a sample presentation apparatus comprising the following steps:

feeding a sample sequentially into said sample presentation apparatus comprising at least one predetermined analysing position;

temporarily fixing said sample at the analysing position in a closed fixing position by means of a two-piece fixing means comprising a first and second sample holding part;

moving said first and second sample holding parts to an open position to allow the sample to be transported to an ejecting position.

The present invention provides for an automated and continuous analysis of samples on-line, from for example a tabletting process, or at-line from for example a batch source of tablets. In contrast to prior art techniques the present invention provides an apparatus for fast and reliable measurements in which there is no need for manual handling of the samples.

The alignment of each sample to be analysed is optimised with respect to achieving high reproducibility of positioning the sample in the same predetermined three-dimensional position in space (x-, y-, and z-co-ordinates), that is relative to the irradiation source beam(s) and detector(s). In this way a high measurement rate, i.e. samples per time unit, is secured.

Further, the same sample presentation system can be used in both at-line and on-line measurement applications.

In a preferred embodiment optical measurement is carried out on the samples. The present invention has the advantage of using at least one two-piece means for fixing each sample in at least one predetermined analysing position and thus the same effective optical aperture will be used in all measurements.

In the open position, none of the first and second sample holding parts of the two-piece means for fixing is in contact with the sample. Instead, the open position allows for shifting the sample to be analysed in the analysing position.

The invention is described in greater detail below with reference to the accompanying drawings, which illustrate the preferred embodiments.

DESCRIPTION OF PREFERRED EMBODIMENTS

Figure 1:
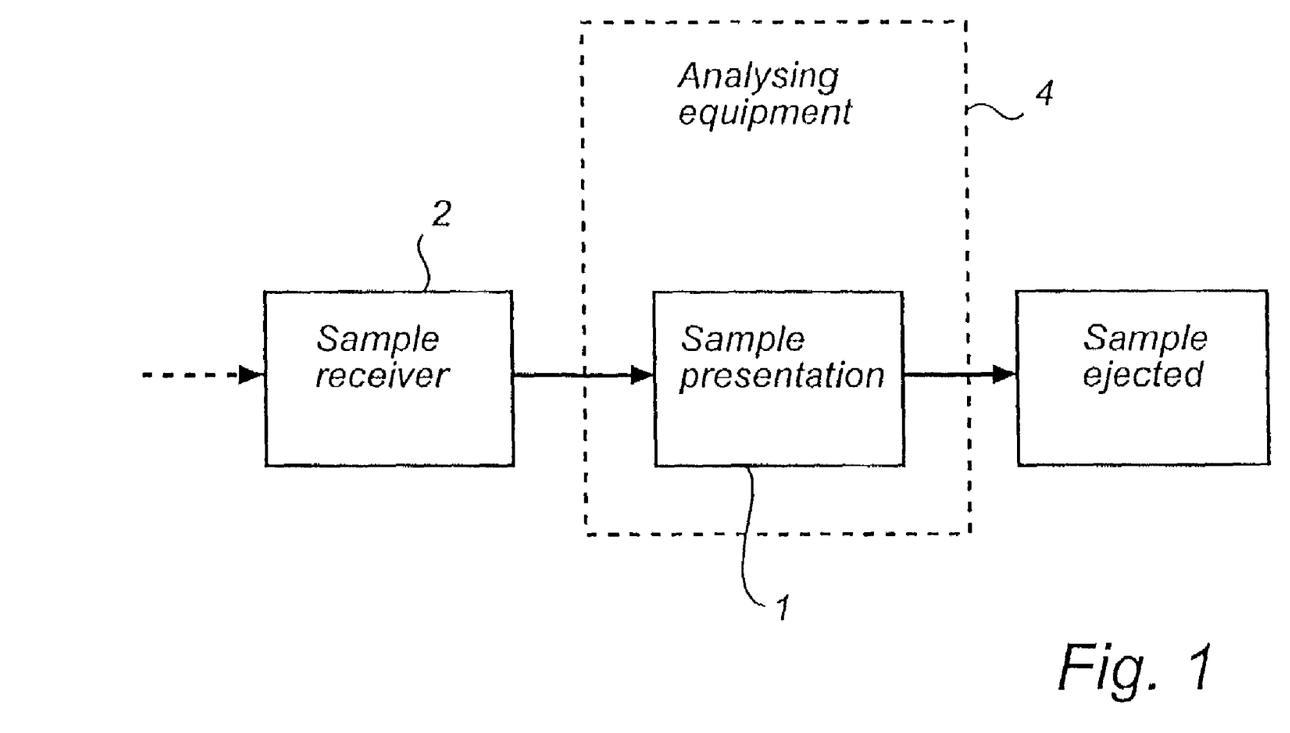
FIG. 1 shows a schematic drawing illustrating the path of a sample through different parts of a sample presentation apparatus according to the present invention.

Referring now to FIG. 1 schematically showing the path of a sample to be analysed in a sample presentation apparatus. A pharmaceutical sample of a solid dosage form, for example a tablet, reaches a sample receiver 2 for further transport to the analysis position in the sample presentation apparatus 1. The sample receiver transports and arranges the samples for sequential queuing and feeds samples further into the sample presentation apparatus. The object of the presentation apparatus is to present a sample to analysing equipment 4 so that a measurement(s) can be carried out on the sample. When the measurements for the analyses are completed the sample is ejected from the sample presentation apparatus.

Figure 2:
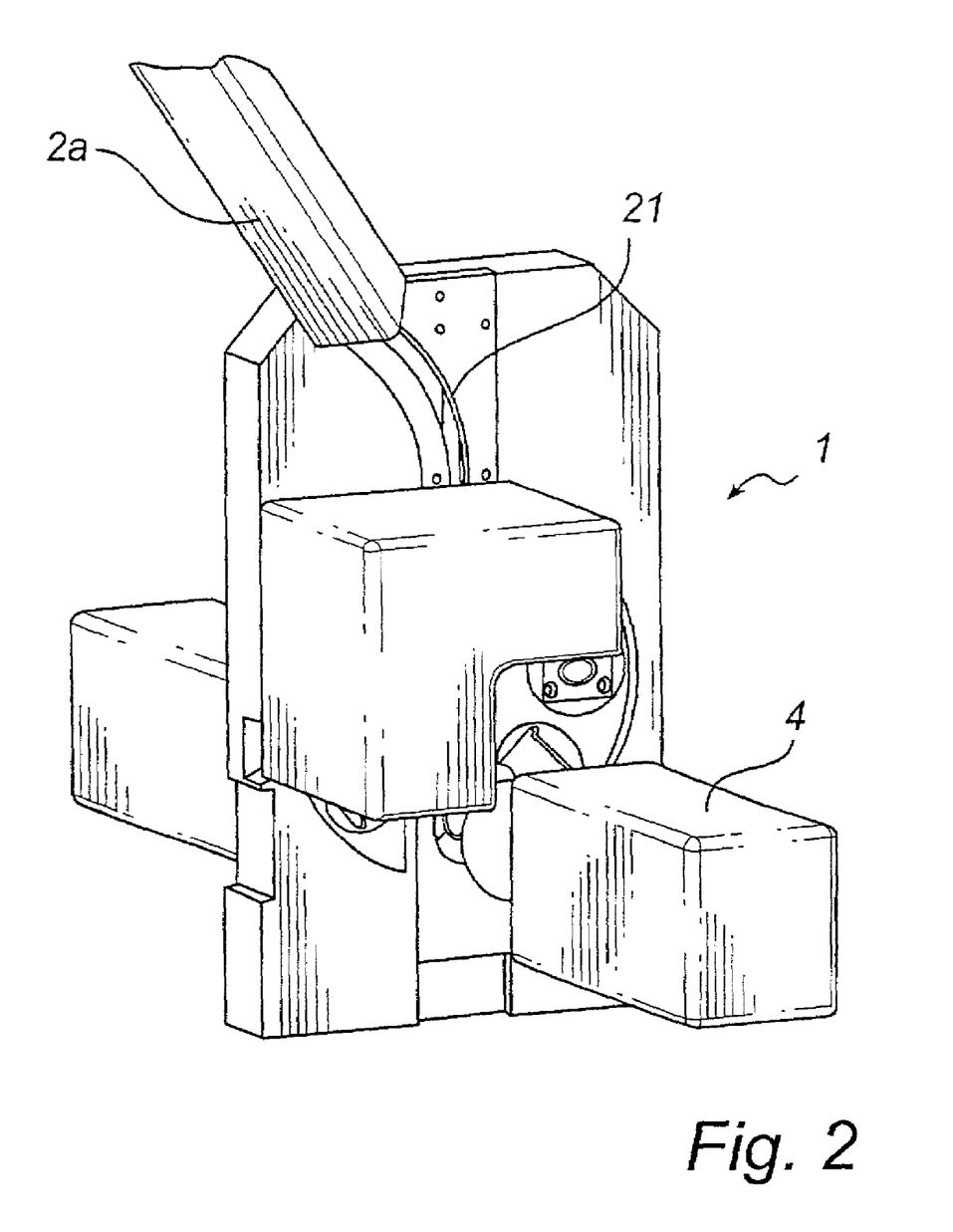
FIG. 2 illustrates a first embodiment of the sample presentation apparatus connected to an on-line sample receiver.
Figure 3:
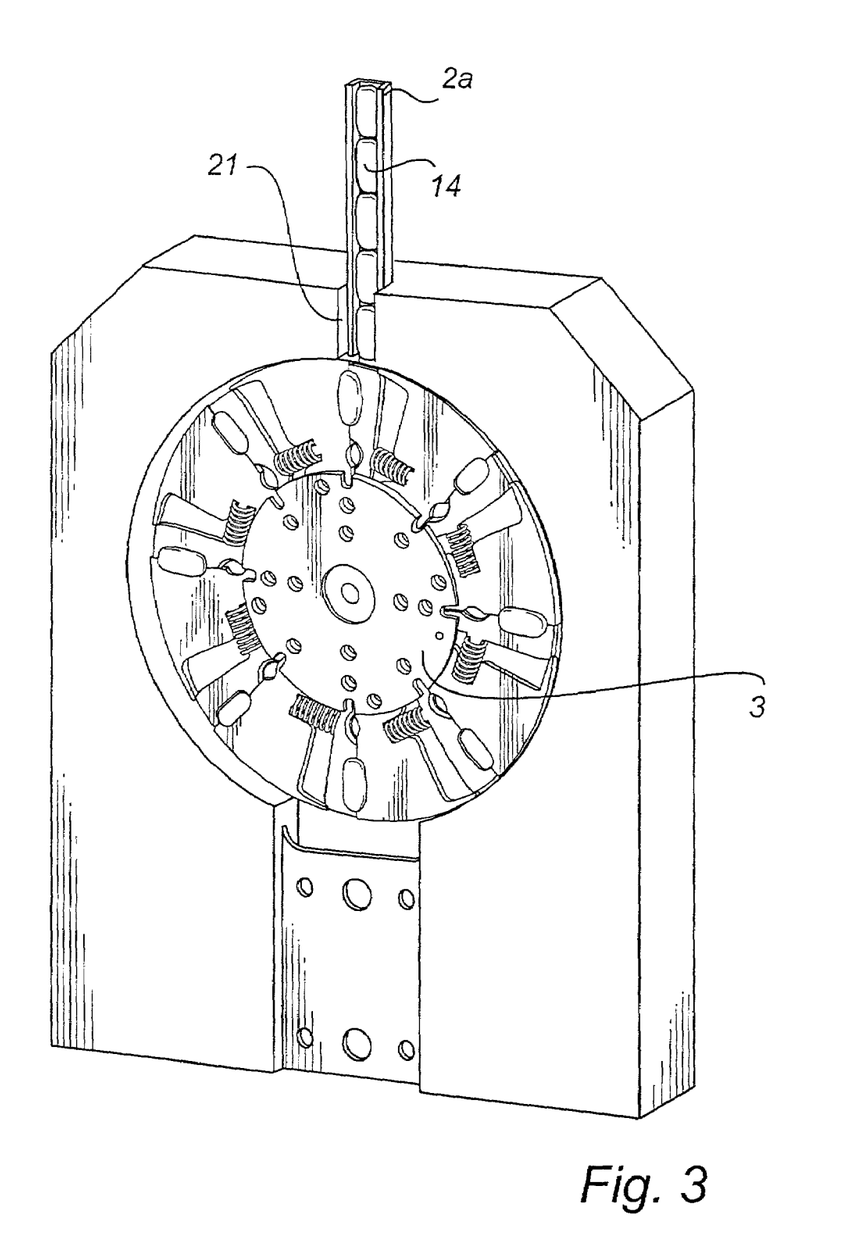
FIG. 3 illustrates another embodiment of the sample presentation apparatus, with some parts removed for clarity, connected to an on-line sample receiver.

In a preferred embodiment the sample receiver 2 is connected on-line, for example to a tablet production line. In the embodiment shown in FIG. 2, a transport line 2a from the tabletting process represents the sample receiver 2. The transport line is connected to a transport slot 21 on the sample presentation apparatus 1. In another embodiment shown in FIG. 3 the transport line 2a connects to a vertical transport slot 21.

Figure 4:
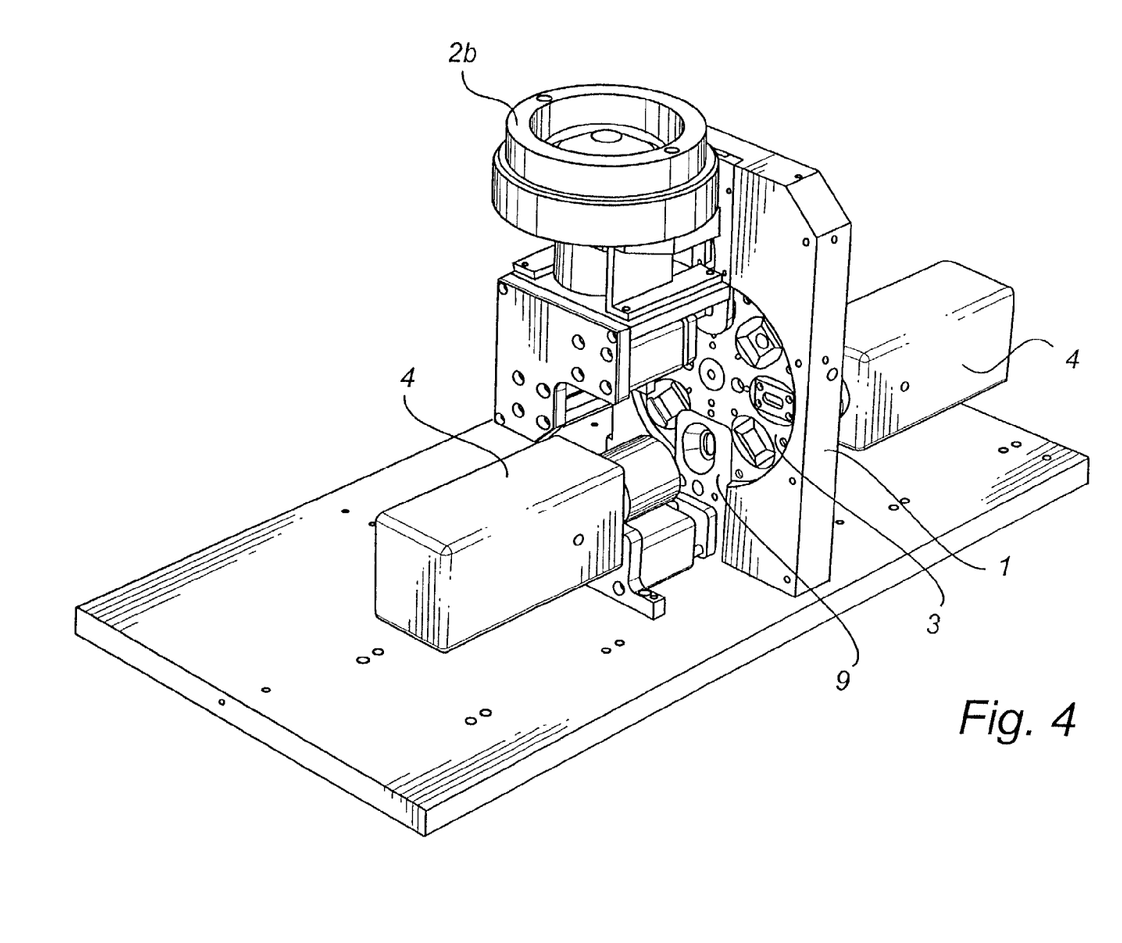
FIG. 4 shows the sample presentation apparatus according to the embodiment of FIG. 2 but connected to an at-line sample receiver.

In a further embodiment shown in FIG. 4 the sample presentation apparatus is arranged for use at-line and thus for receiving samples from a batch source, for example samples withdrawn from a tabletting process. The apparatus is connected to an at-line sample receiver 2b. The at-line sample receiver 2b will be described in detail below with reference to FIG. 11.

Figure 5:
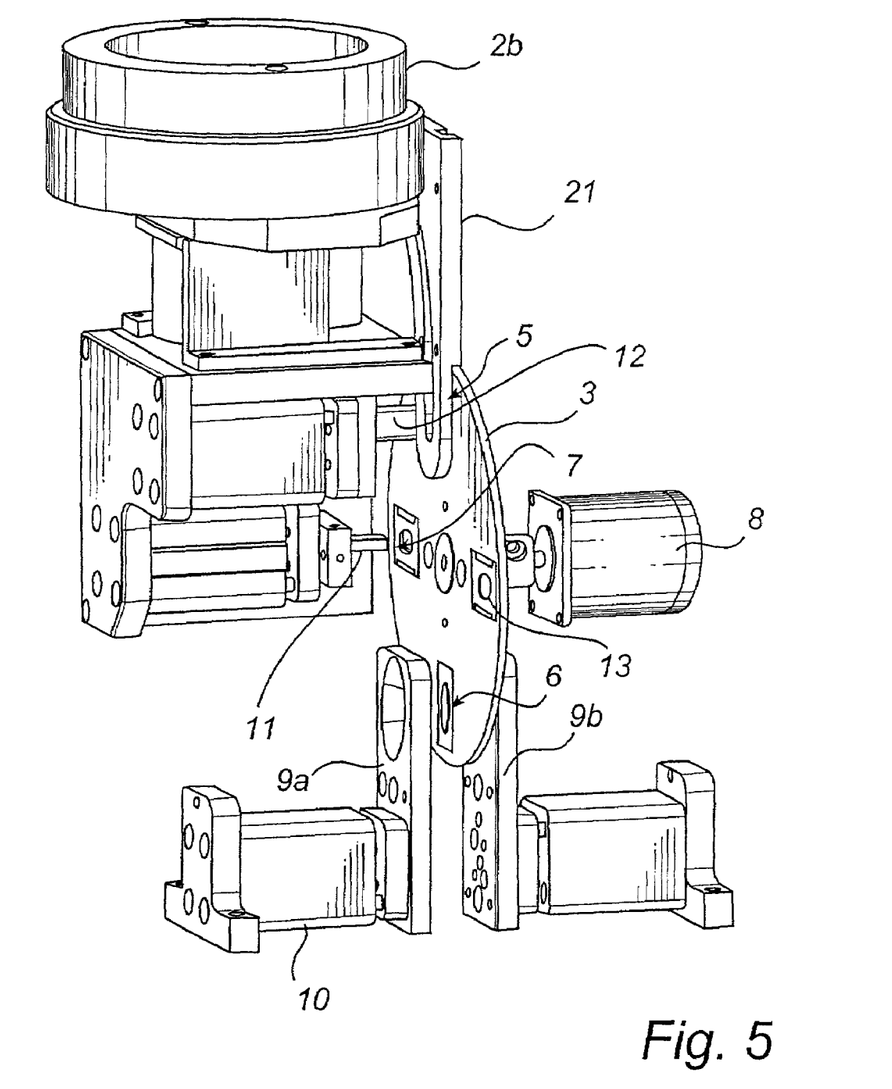
FIG. 5 shows the sample presentation apparatus according to FIG. 4 with some parts removed for clarity.

The sample presentation apparatus is illustrated in FIG. 5 wherein some parts have been removed for clarity. The radiation generating unit, the radiation detecting unit, the means for controlling mechanical movements and the means for receiving and evaluating the detector output can be implemented in many ways and are not described in detail in this application. The sample presentation apparatus 1 comprises means for feeding samples sequentially through the analysing position 6 and said feeding means comprises at least one pre-alignment means 13 for receiving and holding a sample 14 during the transport thereof to the predetermined analysing position 6. In a preferred embodiment, the feeding means is represented by a rotating wheel 3 illustrated in FIGS. 9 and 10. However, the invention is not restricted to this embodiment. A linearly operating feeder mechanism could also be used, as well as a reciprocating feeder mechanism. Still, the illustrated embodiment has the advantage of allowing a fast analysing process, e.g. enabling in-line sample measurements from for example a tablet production line.

The analyses of the samples take place in at least one predetermined analysing position 6 in the sample presentation apparatus wherein a sample is temporarily fixed while the measurement is performed. A two-piece means for fixing the sample at the analysing position comprising a first and a second sample holding part encloses the sample in the analysing position.

Figure 6:
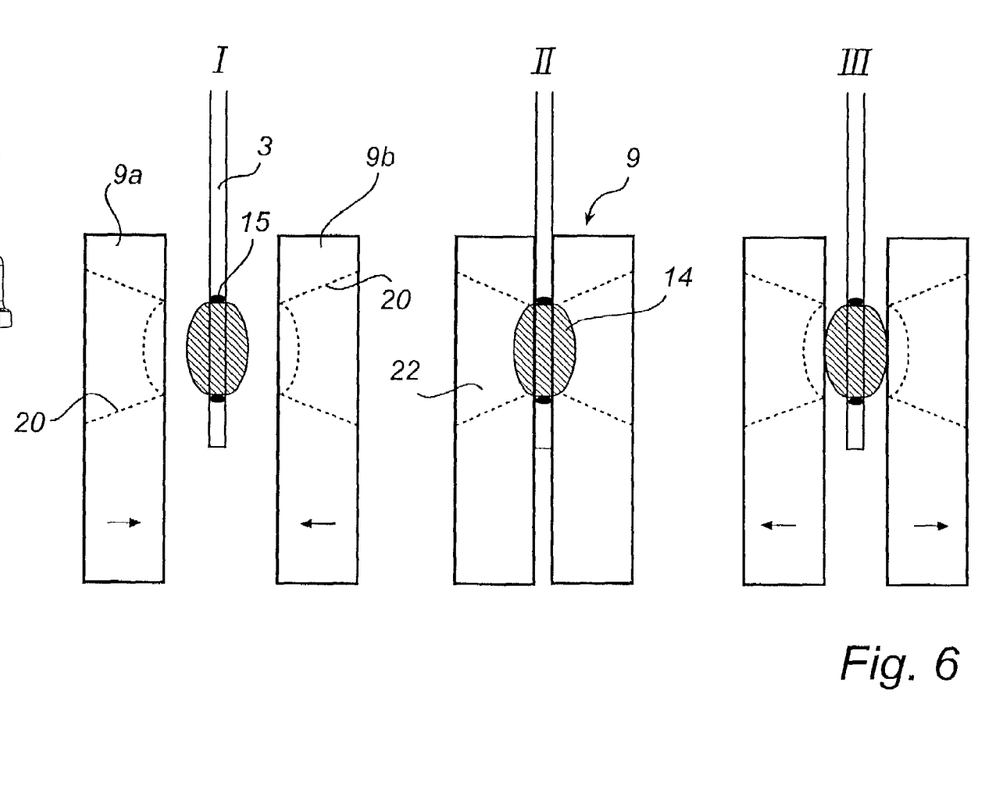
FIG. 6 illustrates the movement of a two-piece sample holder according to a preferred embodiment.
Figure 7:
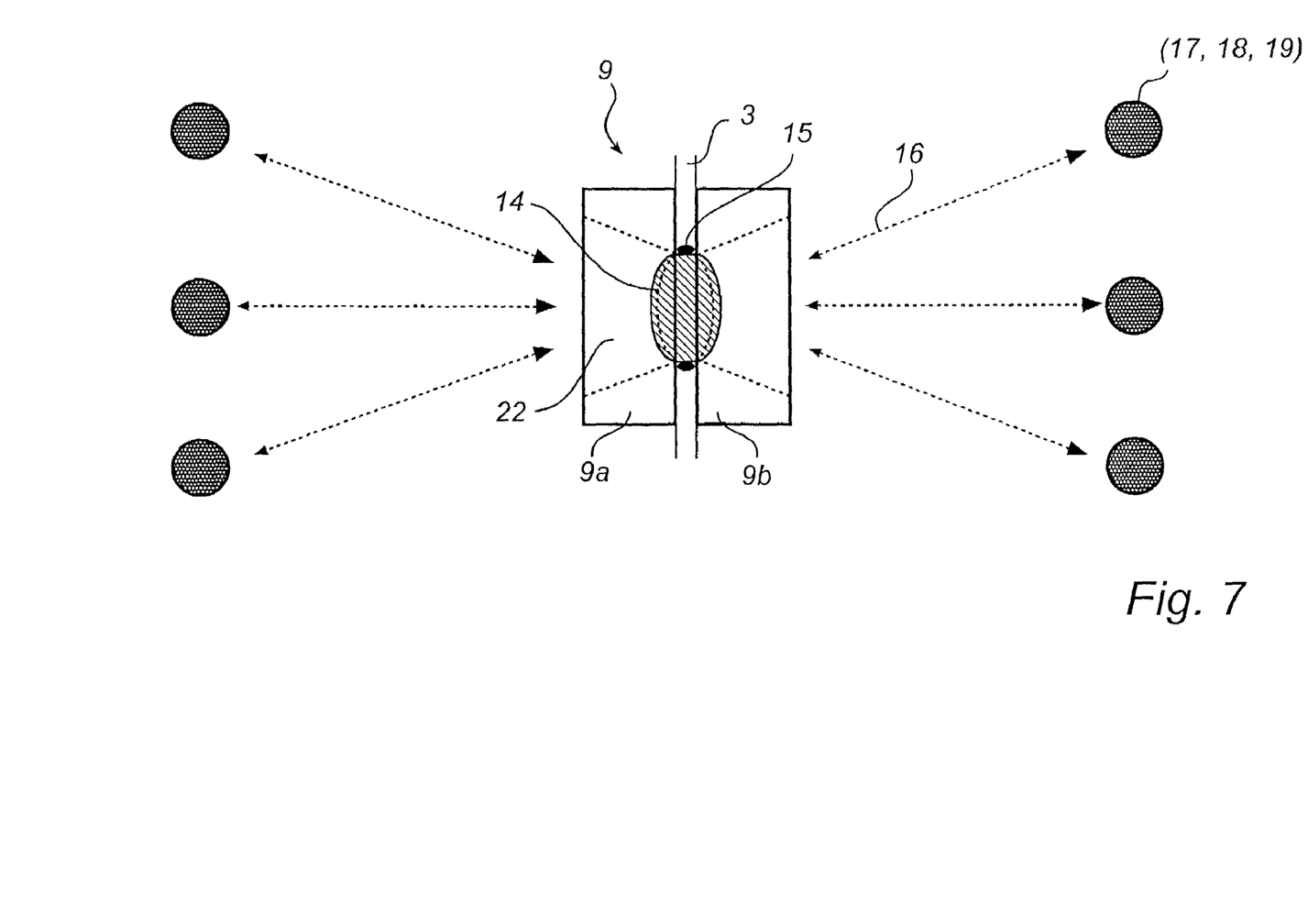
FIG. 7 shows a top view of the two-piece sample holder according to FIG. 6 and possible beam paths.

In FIGS. 5, 6 and 7 a preferred embodiment of a two-piece means for fixing 9 is illustrated.

Figure 8:
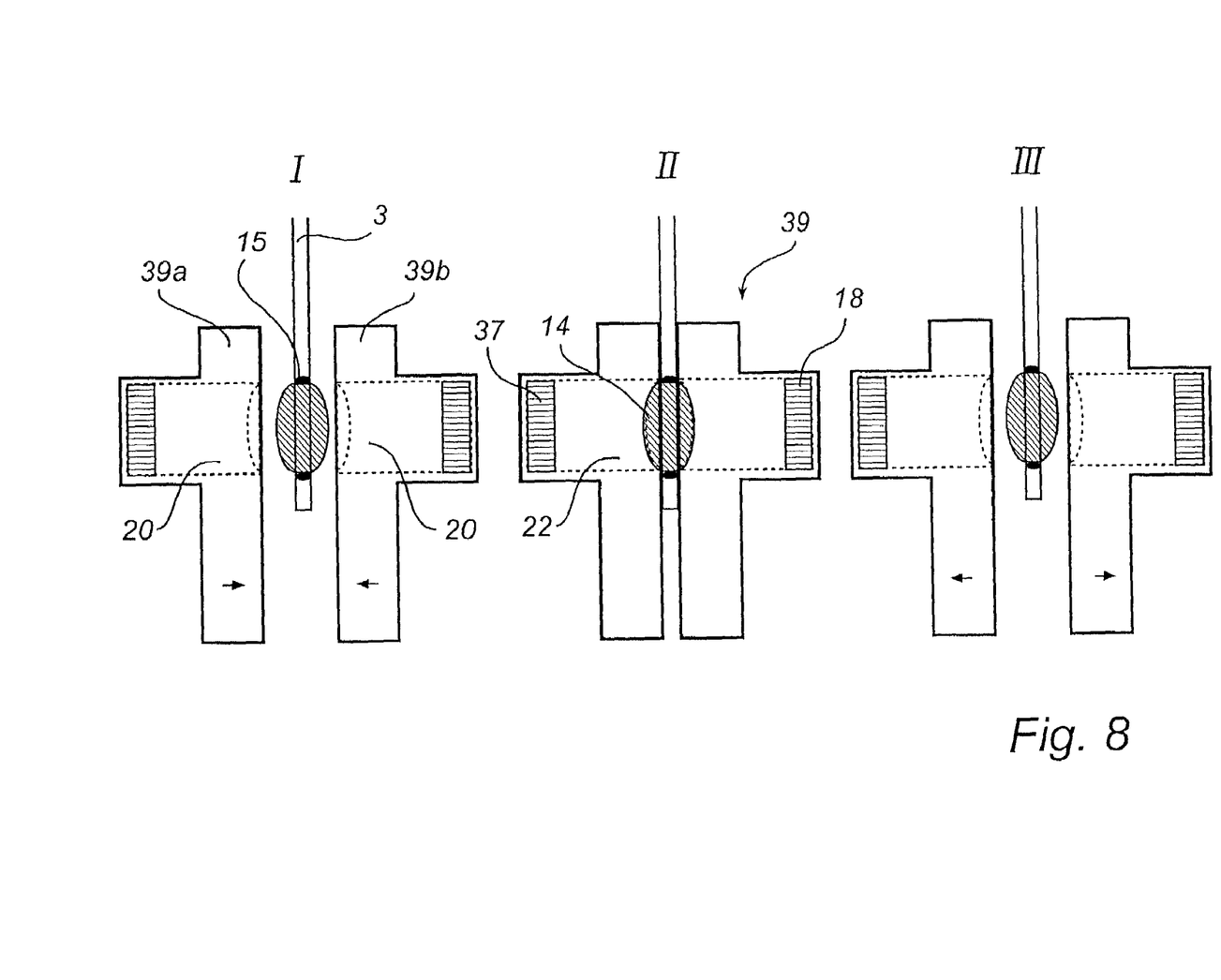
FIG. 8 illustrates the movement of a two-piece sample compartment according to another embodiment.

In another embodiment shown in FIG. 8, the two-piece means for fixing 39 is designed to constitute a closed compartment having a fixed volume around the sample 14. This embodiment is applicable for measurements using microwave radiation and detection. The predetermined volume is set to fit the frequency of radiation used in the measurements. A microwave source 37 is positioned in one the sample holding compartments 39*a*, 39*b*.

The samples are transported as the wheel rotates about its central axis, which is connected to a stepping motor 8 and the rotation is performed in discrete steps. In FIG. 5, the feeder wheel 3 is rotated by 90 degrees for each sample analysing step. However, steps of 45 degrees or other may also be used. As the wheel 3 rotates in discrete steps to present a sample to the analysing position 6, each pre-alignment means 13 passes three different positions within the sample presentation apparatus:

1) a sample receiving position 5,
2) an analysing position 6, and
3) a sample ejecting position 7.

The three positions are illustrated in FIG. 5. However, the invention is not restricted to a single analysing position. Two analysing positions could also be used. In this way a sample may first be subject to an IR-measurement and then be subject to a measurement using microwaves;

Samples are provided from a transport slot 21 to the sample receiving position 5 and one sample at a time is then inserted into the pre-alignment means 13 by pneumatic loading means 12.

Figure 9:
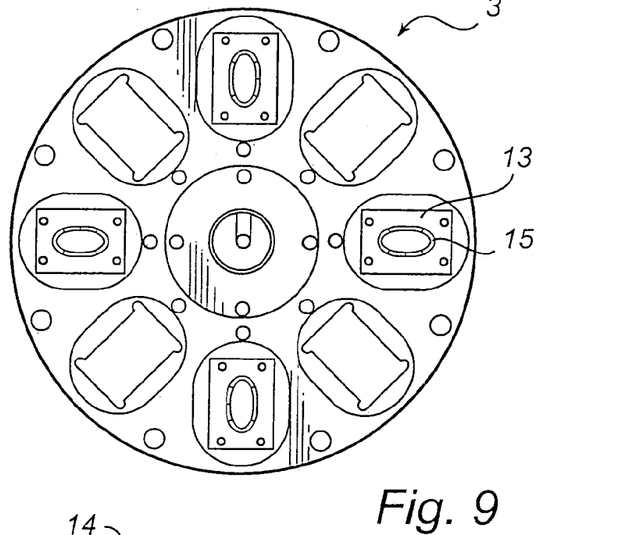
FIG. 9 illustrates a feeder means comprising pre-alignment means according to a first embodiment.

In the embodiment shown in FIG. 9 the loading means pushes a sample into a pre-alignment means 13. In the embodiment illustrated in FIG. 10 the loading means actiates a spring-loaded arm 31 such that the pre-alignment means is opened up for receiving a sample 14 in the pre-alignment 13 through the periphery of the feeder wheel 3.

At the analysing position 6 the sample is temporarily fixed between a first and a second sample holding part 9*a*, 9*b*, 39*a*, 39*b*. In a preferred embodiment the sample holding parts each has an aperture 20 to define a beam path 16 through the sample subjected to an optical measurement.

In the ejecting position 7 the sample is ejected by pneumatic ejecting means 11. The empty pre-alignment means 13 now proceeds to receive a new sample.

At the analysing position 6, the two-piece means of fixing 9, 39 encloses the sample 14 and secures that a plurality of samples are sequentially presented to the analysing equipment in a precise and standardised three-dimensional position. The two-piece means 9, 39 comprises a first 9*a*, 39*a* and a second 9*b*, 39*b* sample holding part. The two parts are movable between an open position wherein a sample, such as a tablet, is provided for analysis and a closed fixing position wherein the tablet is analysed.

It is important that each sample arrives at the analysing position having a certain three dimensional orientation. Therefore, each sample is pre-aligned in the feeder wheel before it reaches the analysing position. However, the engagement in the pre-alignment means is sufficiently flexible to allow the sample holding parts to accomplish a final adjustment of position in the analysing position.

In one embodiment the feeder wheel presents a plurality (four in this embodiment) of circumferentially spaced pre-alignment means. Each pre-alignment means is arranged to hold a sample in a flexible fashion such that the position and orientation of the sample received in a given pre-alignment means are maintained during the movement from the sample receiving position to the analysing position. Each pre-alignment means comprises a rectangular insert to be mounted in an aperture in the feeder wheel 3. The rectangular insert is provided with an opening for receiving a sample, which opening is lined with an elastically compressible member. Preferably, the opening is lined with a flexible rubber ring 15. The function of the flexible ring 15 is to maintain a sample in the position and orientation as obtained at the receiving position 5. The function of the flexible ring is also to seal against the outer periphery of the sample and to minimize stray radiation.

Figure 10:
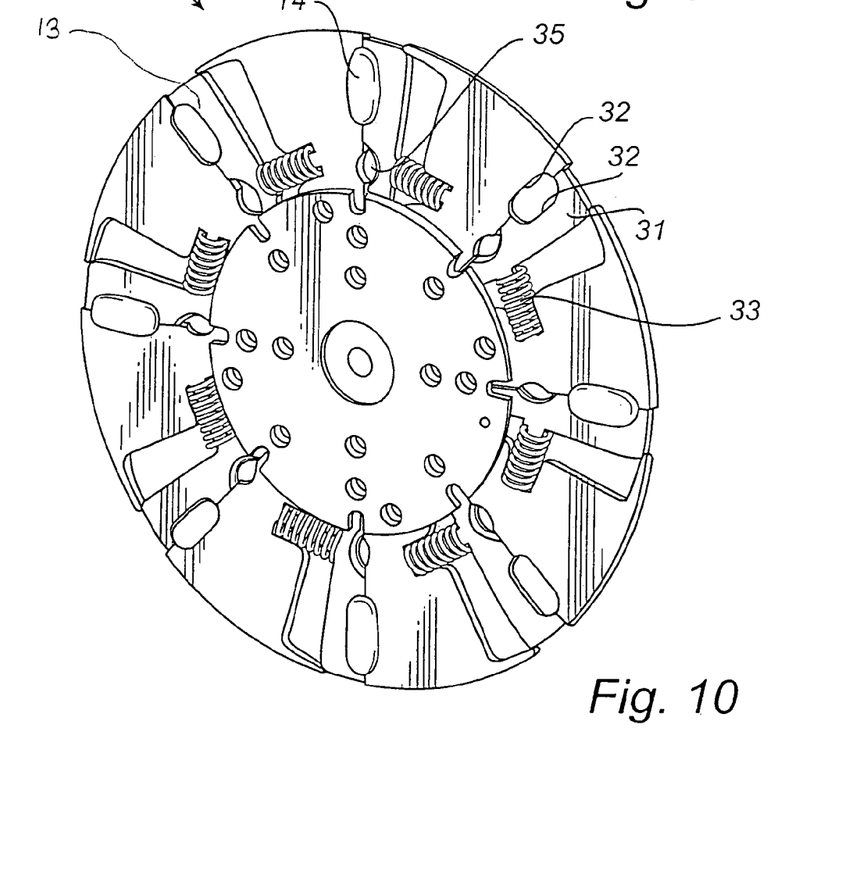
FIG. 10 illustrates a feeder means comprising pre-alignment means according to a second embodiment.

In another embodiment, each pre-alignment means 13 comprises a more or less rectangular opening in the feeder wheel 3 and a spring-loaded arm 31 to be mounted in the opening. When the spring 33 connected to the arm 31 is actuated the arm is moved within the rectangular opening in the feeder wheel and an opening is formed in the periphery of the wheel through which a sample enters the pre-alignment means 13. The spring-loaded arm 31 and a part of the feeder wheel 3 respectively, are provided with an indentation 32. These two indentations form a space for receiving a sample 14, such that the spring-loaded arm 31 from one end and a part of feeder wheel from the other embraces a sample. The spring loaded arm is actuated upon by a pneumatic loading means 12 that is introduced into a groove 35 in the feeder wheel and the arm 31 is moved to one side and a sample is received through the periphery of the feeder wheel 3. Preferably, the indentations 32 in the arm and in the wheel 3 can be designed to receive different sizes of samples. After the measurement has been carried out in the analysing position 6 the sample is transported to the ejecting position 7 to be ejected by the pneumatic ejecting means 11.

Referring now to FIGS. 5 and 6, the sample fixing means comprises first 9*a* and a second 9*b* sample holding parts. In this preferred embodiment for performing an optical measurement, the two parts 9*a*, 9*b* each have an aperture 20 so as to expose each side of the sample to the measuring beam(s). By means of the pre-alignment means 13 in the wheel 3, the sample now has reached its final alignment relative to a measurement optical axis(es) at the analysing position 6. Each tablet holding part 9*a*, 9*b* is movable by pneumatic means 10.

The analysing position 6, a sample is temporarily fixed between the first 9*a*, 39*a* and the second 9*b*, 39*b* sample holding parts. The sample holding parts each has an aperture 20 that, when enclosing a sample 14, together constitutes the effective optical aperture 22 for the measurement(s). That is, when the holders are joined and firmly enclose the sample snugly, they define the delimited beam path 16 for radiation through the sample 14 that is subjected to the optical measurement(s). In FIG. 7, the analysing equipment 4 is schematically shown as dark circles illustrating radiation source(s) 17, detector(s) 18 and/or camera(s) 19. In this way the same effective aperture 22 is used for all samples to be analysed, whereby the precision is significantly improved compared with known prior art.

Reference is now made to FIG. 6 or FIG. 8 of the drawings. The first 9*a*, 39*a* and second 9*b*, 39*b* sample holding parts are adapted to move between a closed fixing position (II) and an open position (I, III). When the two parts are moved towards each other to enclose an intermediate sample 14, they are moved into the closed fixing position (II). In this position the measurement takes place. After the measurement, the two parts are moved away from each other to release the sample. The sample holding parts are thus moved into the open position. As the two sample holding parts move away from each other the wheel 3 is stepped forward to present a new sample to be analysed in the analysing position 6. The sample, still in the pre-alignment means 13, continues with the wheel to the ejecting position 7 where the sample is ejected.

Preferably, the optical measurement is performed by means of near-infrared (NIR) spectrometry and/or a spectrometric method based on Raman scattering and/or a spectrometric method based on absorption in the UV, visible, or infra-red (IR) wavelength region, or luminescence, such as fluorescence spectrometry, or based on X-ray. Here, measurements can be conducted in the reflectance and/or the transmission mode. The measurement can also be performed by means of imaging using any of these spectrometric techniques. Further, measurements can also be based on microwave technology.

Figure 11:
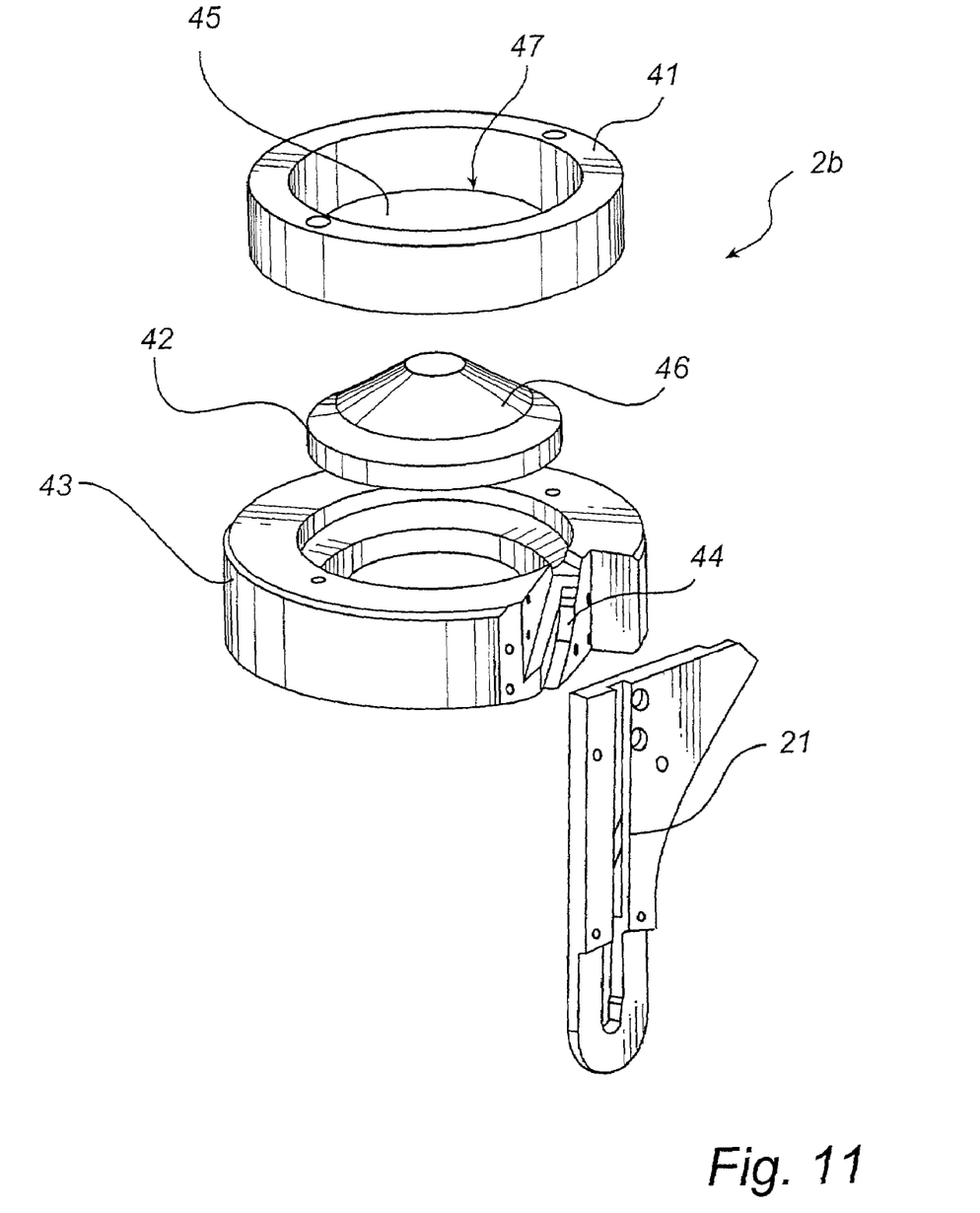
FIG. 11 shows an exploded view of the at-line sample receiver according to a first embodiment.

Reference is now made to FIG. 11 illustrating the second embodiment of the sample receiver 2. The sample receiver is arranged to line up the samples in a queue before they enter the sample presentation apparatus. The at-line sample receiver 2b comprises a conical shaped rotating part 42 that constitutes the bottom of an open vessel 43 with a cylindrical geometry. The vessel has a ring as a partially open top lid 41 wherein the opening is located in the centre of the lid. Through the top opening 45 samples are poured into the receiver and the samples fall upon the rotating cone which, due to its rotation and its sloping surface, guides the samples towards the base or periphery of the cone 42. The rotating cone is preferably non-vibrating in order not to influence the optical measurement.

The functionality of the receiver is based on the fact that samples, for example tablets or capsules, typically have an advantageous and well-defined geometry. That is, the length, width and thickness of a specific sample type are not all identical. In this way orientation and sorting for queuing of samples can be conducted by means of centre of gravity relations and gravity. Indeed, the function of the receiver only requires that two of these sample measures are at least slightly different. Thus, the receiver will work with common types of tablet and capsule geometries. The detailed functionality is described in the following section.

From a batch source or from a production line, tablets are fed into the open top 45 lid of the at-line sample receiver. The tablets fall down alongside the rotating cone 42. Through rotation, by means of friction from the surface 46 of the cone and by gravity, samples are forced to lie flat and are forced towards the outer periphery of the cone 42. Further, sorting and queuing up is accomplished through utilising a slit like opening between the surface 46 of the cone and the lower inner edge 47 of the top lid. The opening has been given a height that is adjusted to precisely fit one of a sample's geometries. In this way, samples are forced all the way down to the outermost periphery of the cylindrical vessel 43, which in turn also constitutes the base of the cone. Samples are thereby lined-up and transported to exit the sample receiver device while having obtained a predetermined orientation. An exit port 44 is located at one position along the bottom periphery of the vessel. Through the exit port 44 samples are fed into a transport slot 4 that connects the sample receiver 2 with the sample presentation apparatus 1.

Figure 12:
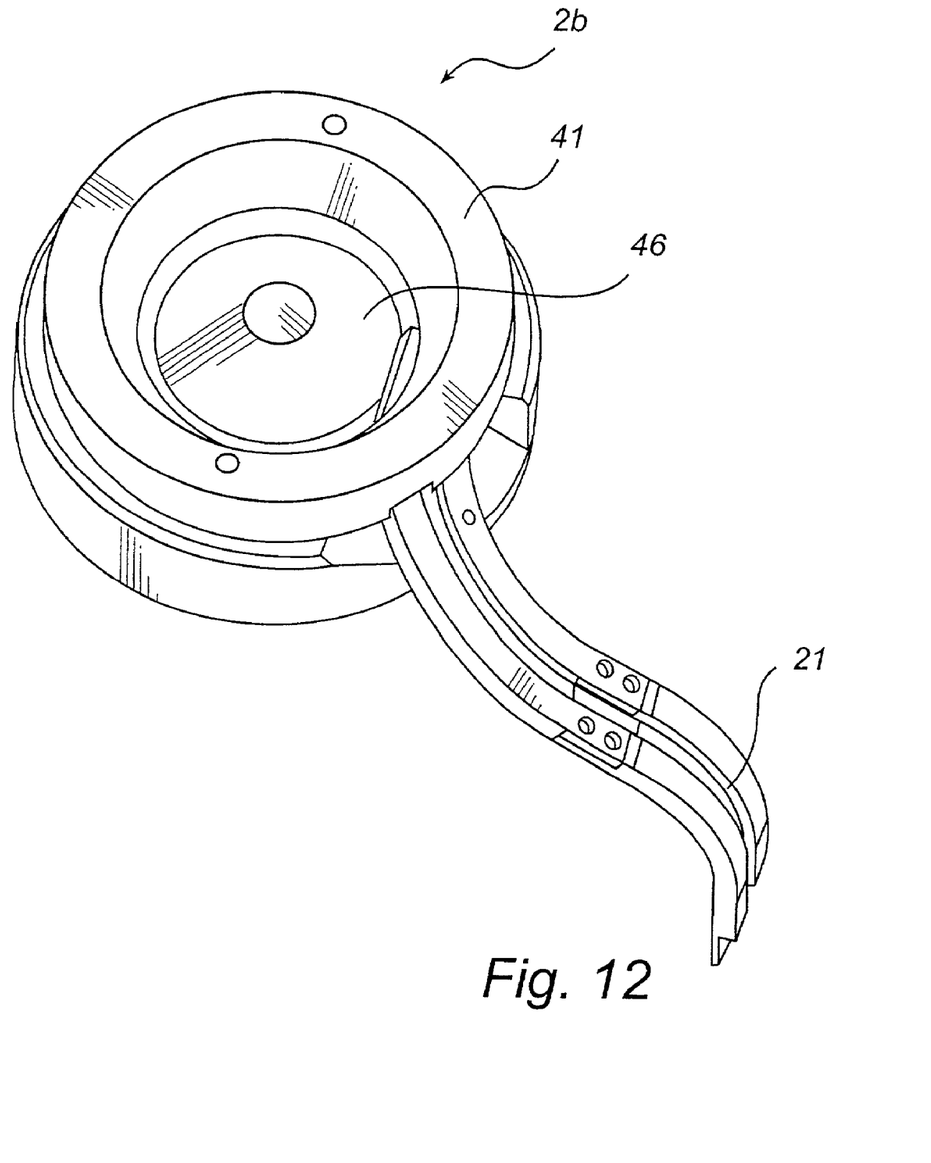
FIG. 12 illustrates the at-line sample receiver having a transport line according to a second embodiment.

In FIG. 12 another embodiment of the sample receiver for use at-line is shown. In this embodiment the transport slot 21 is connected to a sample presentation apparatus 1 using the rotating wheel 3 according to FIG. 10 wherein the samples reaches the pre-alignment means 13 through the periphery of the wheel 3.

Finally, it will be understood by a person skilled in the art that the present invention is not limited to the described embodiments but can be modified in many different ways within the scope of the appended claims.

The invention claimed is:

1. An apparatus for use in analysing pharmaceutical samples, comprising:
   (a) means for feeding one or more samples through at least one predetermined analysing position, wherein at least one measuring radiation beam irradiates the sample when the sample is located at the analysing position; and
   (b) means for temporarily fixing the sample at the analysing position, wherein the fixing means comprises a first and a second holding part, wherein the first holding part defines a first aperture in said first holding part, and the second holding pan defines a second aperture in said second holding part, and the first and second apertures together define an effective optical aperture in the closed position, and;
   wherein the holding parts open at the analysing position to receive the sample from the feeding means and close at the analysing position for analysis.

2. A method for presenting pharmaceutical samples to the apparatus according to claim 1, the method comprising the steps of:
   (a) feeding a sample to the holding parts which are open at the analysing position for receiving the sample from the feeding means;
   (b) temporarily fixing the sample at the analysing position in a closed fixing position by closing the first and second holding parts; and
   (c) moving the first and second holding parts to an open position to allow the sample to be transported to an ejecting position.

3. An apparatus for use in analysing pharmaceutical samples, comprising:
   (a) means for feeding one or more samples through at least one predetermined analysing position, wherein at least one measuring radiation beam irradiates the sample when the sample is located at the analysing position; and
   (b) means for temporarily fixing the sample at the analysing position, wherein the fixing means comprises a first and a second holding part, and wherein the holding parts open at the analysing position to receive the sample from the feeding means and close at the analysing position for analysis.

4. A method for presenting pharmaceutical samples to the apparatus according to claim 3, the method comprising the steps of:
   (a) feeding a sample to the holding parts which are open at the analysing position for receiving the sample from the feeding means;
   (b) temporarily fixing the received sample at the analysing position by closing the first and second holding parts; and
   (c) moving the first and second holding parts to an open position to allow the sample to be transported to an ejecting position.

5. The method according to claim 2 or 4, wherein a measurement is performed by irradiating the sample with at least one measuring radiation beam while the sample is being temporarily fixed at the analysing position.

6. The method according to claim 5, wherein the measurement is an optical measurement.

7. The method according to claim 6, wherein the optical measurement is carried out by means done or more spectroscopic methods selected from the group consisting of near-infrared (NIK) spectrometry, Raman scattering spectrometry, absorption in the UV, visible, or infra-red (IR) wavelength regions, luminescence spectrometry, fluorescence spectrometry, and X-ray spectrometry.

8. The method according to claim 7, wherein the optical measurement is carried out by means of one or more spectroscopic imaging methods selected from the group consisting of near-infrared (NIR) spectrometric imaging, Raman scattering spectrometric imaging, imaging based on absorption in the UV, visible, or infra-red (IR.) wavelength regions, luminescence spectrometric imaging, fluorescence spectrometric imaging, and X-ray spectrometric imaging.

9. The method according to claim 5, wherein the radiation beam is a microwave beam.

10. The apparatus according to claim 1 or 3, wherein the first and second holding parts are located on opposite sides of the sample when in the closed position.

11. The apparatus according to claim or 3, wherein die first and second holding parts do not contact the sample in the open position.

12. The apparatus according to claim 1 or 3, wherein the first and second holding parts each define a first and second compartment which together define a predetermined volume.

13. The apparatus according to claim 1 or 3, wherein the means for feeding samples through the analysing position comprises at least one pre-alignment means for receiving and holding a sample during transport of the sample to the analysing position.

14. The apparatus according to claim 13, wherein the pre-alignment means comprises an elastically compressible member for flexibly engaging the sample.

15. The apparatus according to claim 14, wherein the elastically compressible member is an elastically compressible ring which in an uncompressed state has an inner dimension which is slightly smaller than an outer dimension of the sample.

16. The apparatus according to claim 13, wherein the pro-alignment means comprises a spring-loaded arm for embracing the sample.

17. The apparatus according to claim 16, wherein the spring-loaded arm and a part of the feeding means are provided with an identification for receiving the sample.

18. The apparatus according to claim 1 or 3, wherein the means for feeding samples through the analysing position is a rotating feeder wheel comprising at least one pre-alignment means for receiving at least one sample.

19. The apparatus according to claim 18, wherein the rotating feeder wheel is connected to a sample receiver which provides the feeder wheel with samples to be analysed.

20. The apparatus according to claim 19, wherein the sample receiver is an on-line sample receiver which provides the pre-alignment means with samples.

21. The apparatus according to claim 20, wherein the sample receiver is a transport line connected on-line to an instrument which performs a tabletting process.

22. The apparatus according to claim 19, wherein the sample receiver is an at-line sample receiver which provides the pre-alignment means with samples.

23. The apparatus according to claim 22, wherein the at-line sample receiver comprises a conical rotating part defining the bottom of an open vessel with cylindrical geometry, wherein samples fall upon the conical rotating part to be sequentially aligned before entering the pro-alignment means in the feeder wheel.

24. The apparatus according to claim 1 or 3, wherein the sample is a solid dosage form.

25. The apparatus according to claim 24, wherein the dosage form is a tablet, pellet, or capsule.

* * * * *

UNITED STATES PATENT AND TRADEMARK OFFICE
CERTIFICATE OF CORRECTION

| | |
|---|---|
| PATENT NO. | : 7,219,568 B2 |
| APPLICATION NO. | : 09/806801 |
| DATED | : May 22, 2007 |
| INVENTOR(S) | : Folestad et al. |

Page 1 of 1

It is certified that error appears in the above-identified patent and that said Letters Patent is hereby corrected as shown below:

<u>Col. 9</u>
Line 8: "done" should read --of one--.
Line 10: "NIK" should read --NIR--.
Line 27: "claim or 3, wherein die" should read --claim 1 or 3, wherein the--.

<u>Col. 10</u>
Line 7: "pro-alignment" should read --pre-alignment--.
Line 11: "identification" should read --indentation--.

Signed and Sealed this

Thirty-first Day of July, 2007

JON W. DUDAS
*Director of the United States Patent and Trademark Office*